United States Patent [19]

Baxter et al.

[11] Patent Number: 4,607,041

[45] Date of Patent: Aug. 19, 1986

[54] ANTIHYPERTENSIVE 2-PHENYL HANTZSCH DIHYDROPYRIDINES

[75] Inventors: Andrew J. G. Baxter, Keyworth; John Dixon, Belton; Thomas McInally, Kegworth; Alan C. Tinker, Loughborough, all of England

[73] Assignee: Fisons plc, Ipswich, England

[21] Appl. No.: 601,389

[22] Filed: Apr. 17, 1984

[30] Foreign Application Priority Data

| Apr. 27, 1983 | [GB] | United Kingdom | 8311520 |
| Apr. 27, 1983 | [GB] | United Kingdom | 8311521 |
| Oct. 15, 1983 | [GB] | United Kingdom | 8327660 |
| Oct. 15, 1983 | [GB] | United Kingdom | 8327661 |
| Dec. 22, 1983 | [GB] | United Kingdom | 8334286 |
| Dec. 22, 1983 | [GB] | United Kingdom | 8334287 |

[51] Int. Cl.[4] ................. A61K 31/445; C07D 211/90; C07D 413/04; C07D 413/14
[52] U.S. Cl. .................. 514/318; 514/356; 514/338; 514/340; 514/336; 546/193; 546/194; 546/268; 546/275; 546/271; 546/321
[58] Field of Search ............. 546/321, 271, 194, 268, 546/193, 275; 424/266; 514/356, 338, 318, 340, 336

[56] References Cited

FOREIGN PATENT DOCUMENTS 2117573 10/1972 Fed. Rep. of Germany ...... 546/321

OTHER PUBLICATIONS

Bossert, F. et al. "4-Aryldihydropyridines" Angew. Chem. Int. Ed. Engl. 20 (1981) pp. 762–769.
Schramm, M. et al., "Novel Dihydropyridines With Positive Inotropic Action", Nature, vol. 303 (Jun. 9, 1983) pp. 535–537.

Primary Examiner—Henry R. Jiles
Assistant Examiner—Dale A. Bjorkman
Attorney, Agent, or Firm—Marshall, O'Toole, Gerstein, Murray & Bicknell

[57] ABSTRACT

There are described compounds of formula I,

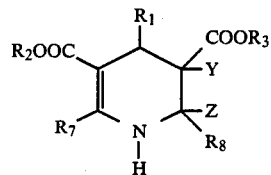

in which $R_1$ represents benzofurazanyl, pyridyl or phenyl, the pyridyl or phenyl being substituted by one or more of the groups halogen, nitro, —CN, —$OR_9$, —$S(O)_pR_9$, or alkyl C1 to 6 optionally substituted by halogen, p is 0, 1 or 2, $R_2$ and $R_3$, which may be the same or different, each represent hydrogen; alkyl C1 to 6 optionally substituted by one or more of the groups halogen, cyano, —$XR_4$, —$NR_5R_6$ or phenyl; cycloalkyl C3 to 8 optionally substituted by alkyl C1 to 6; a 4, 5 or 6 membered oxygen or nitrogen containing heterocyclic ring which is optionally substituted by alkyl C1 to 6 the alkyl in turn optionally being substituted by one or more phenyl groups;

$R_5$ and $R_6$, which may be the same or different, each represent alkyl C1 to 6 optionally substituted by phenyl, Y and Z together form a bond, and additionally, when $R_8$ is an electron withdrawing group Y may be hydrogen and Z may be hydroxy, one of $R_7$ and $R_8$ represents alkyl C1 to 6 and the other represents phenyl, or $R_7$ and $R_8$ may be the same or different and each represents phenyl optionally substituted by one or more of alkyl C1 to 6, halogen, alkoxy C1 to 6 or nitro; amino; alkyl C1 to 6 substituted by halogen; —CN; —$CH_2OH$; —CHO or —$CH(OR_9)_2$, X is O or S, $R_4$ is alkyl C1 to 6 or phenyl, $R_9$ is alkyl C1 to 6, with certain provisons.

There are also described processes for making the compounds, and their formulation and use as pharmaceuticals for treatment of hypertension, angina, or congestive heart failure.

7 Claims, No Drawings

ANTIHYPERTENSIVE 2-PHENYL HANTZSCH DIHYDROPYRIDINES

This invention relates to new compounds, methods for their preparation and compositions containing them.

A wide variety of dihydropyridines have been described as being useful as pharmaceuticals and some, notably nifedipine, have been sold for this use.

We have now found a new group of pyridine derivatives which have pharmacological activity.

According to the invention we provide compounds of formula I,

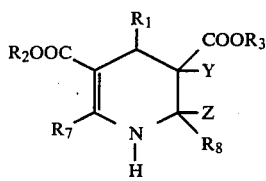

in which $R_1$ represents benzofurazanyl, pyridyl or phenyl, the pyridyl or phenyl being substituted by one or more of the groups halogen, nitro, —CN, —$OR_9$, —$S(O)_pR_9$, or alkyl C1 to 6 optionally substituted by halogen, p is 0, 1 or 2, $R_2$ and $R_3$, which may be the same or different, each represent hydrogen; alkyl C1 to 6 optionally substituted by one or more of the groups halogen, cyano, —$XR_4$, —$NR_5R_6$ or phenyl; cycloalkyl C3 to 8 optionally substituted by alkyl C1 to 6; a 4, 5 or 6 membered oxygen or nitrogen containing heterocyclic ring which is optionally substituted by alkyl C1 to 6 the alkyl in turn optionally being substituted by one or more phenyl groups;

$R_5$ and $R_6$, which may be the same or different, each represent alkyl C1 to 6 optionally substituted by phenyl, Y and Z together form a bond, and additionally, when $R_8$ is an electron withdrawing group Y may be hydrogen and Z may be hydroxy, one of $R_7$ and $R_8$ represents alkyl C1 to 6 and the other represents phenyl, or $R_7$ and $R_8$ may be the same or different and each represents phenyl optionally substituted by one or more of alkyl C1 to 6, halogen, alkoxy C1 to 6 or nitro; amino; alkyl C1 to 6 substituted by halogen; —CN; —$CH_2OH$; —CHO or —$CH(OR_9)_2$, X is O or S, $R_4$ is alkyl C1 to 6 or phenyl, $R_9$ is alkyl C1 to 6, provided that (A)
  (i) when $R_7$ is alkyl C1 to 6, Y and Z together form a bond, $R_1$ represents 3-nitrophenyl and $R_2$ and $R_3$ are both ethyl, then $R_8$ does not represent phenyl,
(B) when neither of $R_7$ and $R_8$ is alkyl C1 to 6, Y and Z together form a bond and
  (ii) $R_2$ and $R_3$ are both ethyl then $R_7$ and $R_8$ are not both —$CF_3$, or
  (iii) one of $R_7$ or $R_8$ is amino then the other is not phenyl or amino, or
  (iv) one of $R_7$ or $R_8$ is —CN, —$CH_2OH$, —CHO or —$CH(OR_9)_2$ then the other is not —CN, —$CH_2OH$, —CHO or —$CH(OR_9)_2$, and
(C) both of $R_7$ and $R_8$ are not optionally substituted phenyl, and pharmaceutically acceptable acid addition salts of those compounds containing a basic nitrogen atom.

According to the invention we also provide the compounds of formula I for use as pharmaceuticals.

According to the invention we further provide a process for the production of a compound of formula I, or a pharmaceutically acceptable acid addition salt thereof, which comprises (a) reaction of a compound of formula II, $$R_1CHO \qquad \text{II}$$

with compounds of formulae III and IV,

$$R_2OOCCH=C(R_7)NH_2 \qquad \text{III}$$

$$R_3OOCCH_2COR_8 \qquad \text{IV}$$

in which formulae $R_1$, $R_2$, $R_3$, $R_7$ and $R_8$ are as defined above, (b) reaction of a compound of formula V, $$R_1CH=C(COOR_3)COR_8 \qquad \text{V}$$

in which $R_1$, $R_3$ and $R_8$ are as defined above, with a compound of formula III, (c) production of a compound of formula I in which Y and Z together form a bond by dehydration of a compound of formula VII,

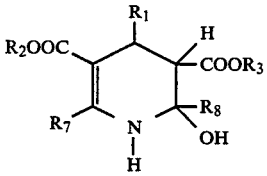

in which $R_1$, $R_2$, $R_3$, $R_7$ and $R_8$ are as defined above, (d) production of a compound of formula I in which p is 1 or 2 by selective oxidation of a corresponding compound of formula I in which p is 0 or 1 respectively, (e) reaction of a compound of formula IV with ammonia and a compound of formula VI, $$R_1CH=C(COOR_2)COR_7 \qquad \text{VI}$$

or reaction of a compound of formula V with ammonia and a compound of formula VII, $$R_2OOCCH_2COR_7 \qquad \text{VII}$$

or reaction of compounds of formulae II, IV and VII with ammonia, in which formulae $R_1$, $R_2$, $R_3$, $R_7$ and $R_8$ are as defined above, (f) production of a compound of formula I in which Y and Z together form a bond and one or both of $R_7$ and $R_8$ is —$CHF_2$ or —$CH_2F$ by reaction of a corresponding compound of formula I in which Y and Z together form a bond and one or both of $R_7$ and $R_8$ is —CHO or —$CH_2L$, where L is —OH or a good leaving group, respectively with a fluorinating agent, (g) production of a compound of formula I in which one of $R_7$ and $R_8$ is —CHO by selective hydrolysis of a corresponding compound of formula I in which one of $R_7$ and $R_8$ is —$CH(OR_9)_2$, (h) production of a compound of formula I in which one of $R_7$ and $R_8$ is —$CH_2OH$ by selective reduction of a corresponding compound of formula I in which one of $R_7$ and $R_8$ is —CHO, (i) production of a compound of formula I in which one of $R_7$ and $R_8$ is —CN by elimination of ROH from a corresponding compound of formula I in which one of $R_7$ and $R_8$ is —CH=NOR, and —OR is a good leaving group, (j) production of a compound of formula I in which at least one of $R_2$ and $R_3$ is hydrogen by reductive cleavage or hydrolysis of a corresponding compound of formula I in which at least one of $R_2$ and $R_3$ is other than hydrogen, (k) production of a compound of formula I in which at least one of $R_2$ and $R_3$ is other than hydrogen by esterification or transesterification of a corresponding compound of formula I in which at least one of $R_2$ and $R_3$ is hydrogen or is a group $R_2$ or $R_3$ other than that desired in the end product, or (l) production of an optical isomer of a compound of formula I by resolution of a mixture of optical isomers of the compound, and where desired or necessary converting the resulting compound of formula I to a pharmaceutically acceptable acid addition salt thereof or vice versa.

The reaction of process (a) may be carried out by subjecting the compounds of formulae II, III and IV to an elevated temperature, e.g. of from about 20° to 140° C. in the presence or absence of a suitable solvent, e.g. a lower alkanol.

Processes (b) and (e) may be carried out under similar conditions to process (a). In processes (a), (b) and (e) when Y and Z in the final product are together to form a bond dehydration is generally required as a separate process step when $R_8$ is an electron withdrawing group, e.g. —$CF_3$, perhaloalkyl-, nitro- or mono- or di-chlorophenyl or unsubstituted phenyl. The presence of a base, e.g. diethylamine or ammonia, tends to inhibit dehydration in these processes. We prefer not to use process (a), (b) or (e) when $R_7$ or $R_8$ is —CN, —$CH_2OH$ or —CHO, or when $R_2$ or $R_3$ is hydrogen.

Process (c) may be carried out in a solvent which is inert under the reaction conditions, e.g. methylene chloride, and in the presence of a dehydrating agent, e.g. trifluoracetic anhydride, and a base, e.g. pyridine. The dehydration may also be effected using diethylaminosulphur trifluoride. The reaction may be carried out at from about 0° to 40° C. The compounds of formula VII may be formed as intermediates, which may or may not be isolated, in processes (a) (b) and (e). Under certain circumstances, e.g. when $R_8$ is not an electron withdrawing group, the compound of formula VII may dehydrate spontaneously to yield the compound of formula I in which Y and Z together form a bond. When diethylaminosulphur trifluoride is used in this process and $R_8$ is $CH_2OH$ or CHO in the starting material the —$CH_2OH$ or —CHO will, as in process (f), be converted to —$CH_2F$ and —$CHF_2$ respectively.

Process (d) may be carried out using a suitable oxidising agent, e.g. peracetic acid. The reaction may be carried out in a suitable solvent, e.g. a mixture of methanol and acetic acid.

Process (f) is preferably carried out at a temperature of from about −70° to 100° C., and in a solvent which is inert under the reaction conditions, e.g. a halogenated hydrocarbon and preferably methylene chloride. The fluorinating agent is preferably a dialkylaminosulphur trifluoride, e.g. diethylaminosulphur trifluoride, or (2-chloro-1,1,2-trifluoroethyl)diethylamine. The group L may be, for example, —$OSO_2Rx$, where Rx is alkyl C1 to 6, e.g. methyl, or aryl, e.g. p-tolyl.

The hydrolysis of process (g) may be carried out using an aqueous acid, for example hydrochloric acid (eg 0.5 to 2.5 molar) in a water miscible organic solvent, e.g. acetone or tetrahydrofuran. The reaction may be carried out at a temperature of from about −10° to 50° C.

The reduction of process (h) may be carried out either chemically or catalytically, e.g. by use of sodium borohydride in an alcoholic solvent, e.g. methanol or ethanol, at a temperature of from about 0° to 50° C.

The elimination of process (i) may be carried out using a variety of dehydrating agents which will not adversely effect the other substituents in the molecule, e.g., an excess of acetic anhydride, thionyl chloride in ether or N,N'-dicylohexylcarbodiimide in pyridine. The group —OR may be, for example, a 2,4-dinitrophenoxy group. The reaction may be carried out at a temperature of from about 0° to 150° C. depending on the reagent and solvent used. The oxime may, if desired, be formed in situ from the corresponding formyl compound using conventional methods known per se.

The reductive cleavage of process (j) may be carried out chemically, e.g. using zinc and formic acid. The reaction may conveniently be carried out in a solvent which is inert under the reaction conditions, e.g. acetonitrile. When process (j) involves a hydrolysis the hydrolysis may be carried out using conventional techniques known per se.

Process (k) may, when it involves an esterfication, be carried out using the appropriate alcohol, preferably in excess and in the presence of a dehydrating agent, e.g. dicyclohexylcarbodiimide. The reaction may conveniently be carried out in a solvent which is inert under the reaction conditions, e.g. ethyl acetate. When a transesterification is involved the process may be carried out by treating the starting ester with the sodium alcoholate corresponding to the desired ester moiety.

The resolution of process (l) may be carried out by means of conversion of the mixture to, when $R_2$ or $R_3$ is H, a salt with an optically active base or an ester with an optically active alcohol (eg $CCL_3(C_6H_5)$ CHOH or $C_6H_5(OCH_3)CHCH_2OH$), or, when $R_2$ or $R_3$ is aminoalkyl, a salt with an optically active acid and separation of the product by selective crystallisation, or, preferably, by means of high performance liquid chromatography (HPLC). The separated product may then be converted to the desired optically active acid or ester by, for example, process (j) or (k).

The starting materials for the above processes are either known, or if they are not specifically known they may be made by processes described in the Examples, or they may be made from known compounds using one or more process steps which are known per se or are analogous to those described in the Examples.

The compounds of formula I and the intermediates therefor may be isolated from their reaction mixtures using conventional processes, e.g. crystallisation or chromatography.

The compounds of formula I, and the pharmaceutically acceptable salts thereof, are useful because they exhibit pharmacological properties in animals. More particularly they block the entry of calcium into vascular and cardiac muscle leading to falls in blood pressure, inotropy and heart rate. They are active in the following systems:

(a) Relaxation of contracted vascular smooth muscle. Van Breemen, Aaronson, Loutzenhiser and Meisheri, Chest, 78, Supplement, 157–165, 1980.

(b) Reduction of inotropy and chronotropy of isolated atria. Henry, Excerpta Med. Int. Congr. Ser., 474, 14–23, 1979.

(c) Reduction of blood pressure and increase cardiac output in anaesthetised dogs. Hirakawa, Ito, Kondo, Watanbe, Hiei, Banno & Hyase, Arzneim-Forsch, 22, 344–349, 1972.

(d) Reduction of blood pressure in conscious dogs when given by the intravenous and oral routes. Newman, Bishop, Peterson, Leroux & Horowitz, J Pharm. Exp. Ther. 201, 723–730, 1977.

The compounds are thus indicated for use in the treatment of renovascular, malignant or essential hypertension (including hypertensive emergencies), pulmonary hypertension, vasospastic angina, chronic stable angina and congestive heart failure. Other indications are the treatment of renal failure, cardiac arrhythmias, hypertrophic cardiomyopathy, cerebrovascular diseases (including cerebral haemorrhage, ischaemia and vasospasm, migraine, altitude sickness and hearing loss), peripheral vascular diseases (including Raynauds syndrome, intermittent claudication and digital ulceration); use as a cardioplegic agent during surgery e.g. in cardiopulmonary bypass, and for the treatment of, and protection against, myocardial infarction and ischaemia.

By virtue of their ability to inhibit calcium entry into other cells and tissues the compounds are also indicated in the treatment of thrombosis, atherosclerosis, respiratory diseases (including asthma and bronchitis) glaucoma, aldosteronism, uterine hypermotility and for the relief of oesophageal and skeletal muscle spasm.

For the above uses the dosage will depend upon the compound used, the route of administration and the effect desired, but in general will be in the range of 0.1–10 mg per kilogram body weight per day. For man the indicated total daily dose will be from about 5–500 mg, preferably from 5 to 200 mg and more preferably from 5 to 100 mg, which may be administered preferably once daily, or in divided doses of about 1–200 mg, preferably 2 to 25 mg, e.g. 2 to 4 times per day.

The compounds of formula I are advantageous in that they possess greater potency (e.g. with respect to hypotensive and direct negative chronotropic effects), produce a lower level of reflex tachycardia, are more selective (e.g. for vascular smooth muscle vs cardiac muscle), produce less depression of cardiac contractility, are longer acting, are more readily absorbed or less readily metabolised, are more easily formulated, possess less, or less undesirable, side effects, are more stable or have other more beneficial properties than known compounds of similar structure.

The compounds of the invention may be administered by a wide variety of routes and may act systemically or locally. Thus the compounds may be administered by oral or nasal inhalation to the lung, to the buccal cavity, oesophageally, rectally, topically to the skin, the eye or to other available surfaces of the body; by injection, e.g. intravenously, intramuscularly, intraperitoneally, or by surgical implant.

When $R_2$ and/or $R_3$ represents a 4, 5 or 6 membered oxygen or nitrogen containing heterocyclic ring that ring may be an oxetanyl, azetidinyl, piperidinyl or tetrahydropyranyl ring. $R_2$ and/or $R_3$ may also represent —$(CH_2)_n XR_4$, —$(CH_2)_n CN$, —$CH(C_6H_5)$ $CCL_3$ or —$(CH_2)_n R_5 R_6$ in which n is 4, 3 or preferably 2.

We prefer compounds of formula I in which Y and Z together form a bond. We also prefer those compounds in which one of $R_7$ and $R_8$ is mono-, di- or trifluoromethyl. We particularly prefer one of $R_7$ and $R_8$ to be mono-fluoromethyl.

Groups $R_8$ which are electron withdrawing include alkyl C1 to 6 substituted by 2 or more halogen atoms; and phenyl optionally substituted by one or more of alkyl C1 to 6, halogen, alkoxy C1 to 6 or nitro. Preferred electron withdrawing significances of $R_8$ are —$CCL_3$, —$CF_3$, —$CF_2$ $CF_3$, phenyl, 4-nitrophenyl, 3,4-dichlorophenyl, 4-chlorophenyl and 3-chlorophenyl.

Values for $R_1$ include nitrophenyl; (trifluoromethyl)-phenyl; mono- or poly-fluorophenyl; mono- or polychlorophenyl; chloro- and/or fluoro-(trifluoromethyl)-phenyl; (alkylthio)pyridyl; alkyl- and/or chloro- and/or alkoxy-nitrophenyl; mixed chloro- and fluoro-phenyl; mono- or poly- alkoxy-phenyl; alkylphenyl; (alkylthio)-phenyl; (alkylsulphonyl)phenyl; and 4-benzofurazanyl. Values for $R_2$ and $R_3$ are alkyl C1 to 4, 2-alkoxy C1 to 3 -ethyl, 2-phenoxy-ethyl, cycloalkyl C4 to 6 optionally substituted by methyl, the saturated 4, 5 or 6 membered heterocyclic groups as defined immediately above and optionally substituted by phenylmethyl or diphenylmethyl, alkyl C1 to 4—(phenylmethyl)aminoethyl, cyano- or alkyl C1 to 4—thioalkyl C1 to 4; phenyl alkyl C1 to 4 or —$CH(C_6H_5)CCL_3$. Values of $R_7$ and $R_8$ are chloro- or fluoro- alkyl C1 or 2, or phenyl substituted by one or two chlorine, nitro, methoxy or methyl groups, e.g. in the 4- and/or 3- positions. $R_7$ and $R_8$ are preferably selected from a fluoromethyl group, e.g. —$CH_2F$, —$CHF_2$ or —$CF_3$; —CHO; —$CH(OC_2H_5)_2$; phenyl and —$CH_2OH$. The Examples illustrate various permutations of substituents. The individual substituents exemplified may also be permutated in other combinations.

As a preferred group of compounds of formula I we provide those in which $R_1$ is phenyl carrying a 2-nitro or a 2—$CF_3$ group or at least two substituents selected from chloro; fluoro; alkyl C1 to 6, e.g. methyl; —$CF_3$ and nitro; $R_2$ is alkyl C1 to 6, e.g. isopropyl, cyclopentyl or cyclobutyl or is oxetan-3-yl; $R_3$ is alkyl C1 to 6, e.g. methyl; $R_7$ is amino, cyano, —CHO or —$CH_2OH$; $R_8$ is fluoromethyl, e.g. mono-, di- or tri-fluoromethyl; and Y and Z together form a bond.

As a most preferred group of compounds of formula I we provide those in which $R_1$ is phenyl carrying at least two substituents selected from chloro, fluoro, —$CF_3$, methyl and nitro, $R_3$ is methyl, $R_7$ is amino, cyano, —CHO or —$CH_2OH$, $R_8$ is —$CH_2F$, $R_2$ is isopropyl or cyclopentyl and Y and Z together form a bond.

As a specific group we provide those compounds of formula I in which $R_1$ is 4-benzofurazanyl, or phenyl substituted by nitro, chloro or —$CF_3$, $R_2$ and $R_3$ are each alkyl C1 to 3 and $R_7$ and $R_8$ are selected from methyl, fluoro- or chloro- alkyl C1 or 2, —CHO, —$NH_2$, —$CH(OC_2H_5)_2$, phenyl optionally substituted by nitro or chloro, —$CH_2OH$ and —CN.

According to our invention we also provide a pharmaceutical composition comprising preferably less than 80%, more preferably less than 50%, e.g. 1 to 20%, by weight of a compound of formula I, or a pharmaceutically acceptable salt thereof, in admixture with a pharmaceutically acceptable adjuvant, diluent or carrier.

Thus the compound may be put up as a tablet, capsule, dragee, suppository, suspension, solution, injection, implant, a topical, e.g. transdermal, preparation such as a gel, cream, ointment, aerosol or a polymer system, or an inhalation form, e.g. an aerosol or a powder formulation.

We prefer compositions which are designed to be taken oesophageally and to release their contents in the gastrointestinal tract. Thus we prefer tablets which may, for example, be made by direct compression. In such a process the active ingredient is mixed with one or more of modified forms of starch, calcium phosphate, a sugar e.g. lactose, microcrystalline cellulose and/or other directly compressible excipients, together with lubricant(s), e.g. stearic acid or magnesium stearate, flow aid(s), e.g. talc or colloidal silicon dioxide, and disintegrant(s), e.g. starch, substituted sodium carboxymethyl cellulose, cross linked sodium carboxy methyl cellulose, carboxy methyl starch and cross linked polyvinylpyrrolidone. Tablets are then formed by direct compression, and may be sugar or film coated e.g. with hydroxypropylmethylcellulose.

Alternatively the active ingredient may be granulated before tabletting. In such cases the active ingredient is mixed with one or more of starch, calcium phosphate, a sugar e.g. lactose, microcrystalline cellulose or other suitable excipients and granulated with a binder such as starch, pregelled starch, polyvinylpyrrolidone, gelatine, a modified gelatine, or a cellulose derivative, e.g. hydroxypropylmethylcellulose. The mass is then dried, sieved and mixed with lubricant(s), flow aid(s) and disintegrant(s), such as described in the previous paragraph. Tablets are then formed by compression of the granules, and may be sugar or film coated, e.g. with hydroxypropylmethylcellulose.

As a further alternative a powder, blend or granules, such as are described above as intermediates in tabletting, may be filled into a suitable, e.g. gelatine, capsule.

In order to improve the bioavailability, or decrease variability of availability, of the active ingredient the compound may be:

(a) dissolved in a suitable solvent, e.g. polyethylene glycol, Gelucaire, arachis oil, a (hydrogenated) vegetable oil or beeswax and the solution is then filled into a gelatine capsule, (b) produced as a spray-dried or freeze-dried form prior to mixing with other excipients, (c) milled and/or micronised to produce a powder with a large surface area prior to mixing with other excipients, (d) made into a solution and distributed over an inert excipient having a large surface area, e.g. colloidal silicon dioxide. The solvent is evaporated and further excipients added, (e) formed into a complex with cyclodextrin prior to mixing with other excipients. This complex also assists in increasing light stability, or (f) made into a solid solution or co-precipitated, e.g. with polyvinylpyrrolidone, polyethyleneglycol, modified cellulose, hydroxypropylmethylcellulose, urea or a sugar prior to mixing with further excipients.

The compounds, either in their normal form or in a modified form, e.g. as described immediately above, may be formulated in a controlled release form. Thus the compound may be dispersed, or contained in, a polymer matrix formed from, for example, ethylcellulose, hydroxypropylmethylcellulose or an acrylate/methacrylate polymer. Alternatively the compound may be formulated as a tablet or beads which are surrounded by a semi-permeable membrane, e.g. shellac, ethylcellulose or an acrylate/methacrylate polymer.

The compounds of this invention may be given in combination with other pharmaceutically active compounds, e.g. diuretics, beta-blockers, antihypertensives or inotropic agents. The dosage of the other pharmaceutically active compound can be that conventionally used when the compound is administered on its own, but is preferably somewhat lower. To illustrate these combinations, a compound of this invention effective in the range, e.g. 5–100 milligrams per day, can be combined at levels ranging, e.g. from 1–200 milligrams per day with the following beta-blockers, antihypertensives and diuretics in dose ranges per day as indicated:

hydrochlorothiazide (15–200 mg), chlorothiazide (125–2000 mg), ethacrynic acid (15–100 mg), amiloride (5–20 mg), furosemide (5–80 mg), propanolol (20–480 mg), timolol (5–50 mg), captopril (10–500 mg), methyldopa (65–2000 mg) or digoxin (0.1–0.5 mg). In addition, the triple drug combinations of hydrochlorothiazide (15–200 mg) plus amiloride (5–20 mg) plus a compound of this invention (3–200 mg) and hydrochlorothiazide (15–200 mg) plus timolol (5–50 mg) plus a compound of this invention (3—200 mg), are provided. The above dose ranges may be adjusted on a unit basis as necessary to permit divided daily dosage. Also, the dose may vary depending on the severity of the disease, weight of patient and other factors which a person skilled in the art will recognise.

Certain of the compounds of formula I are assymetric and exhibit optical isomerism. Such compounds may be separated into their optical isomers using process (p) or may be made by stereospecific syntheses using conventional techniques know per se.

The invention therefore provides the compounds as their individual optical isomers (we prefer the (+) isomers), and racemic or other mixtures of the individual isomers.

In those compounds in which Y is hydrogen and Z is —OH there will be at least 3 assymetric carbon atoms and the corresponding number of isomers is provided.

Certain of the compounds of the invention can form solvates, e.g. hydrates or alcoholates, and certain of the compounds are light sensitive and should therefore be produced, handled, stored and formulated in such a manner that they are not subjected to degrading amounts of light of the appropriate wavelengths.

The invention is illustrated, but in no way limited by the following Examples in which temperatures are in degress centigrade.

EXAMPLE 1

Diethyl 1,2,3,4-tetrahydro-2-hydroxy-6-methyl-4-(3-nitrophenyl)-2-(trifluoromethyl)-3,5-pyridine-dicarboxylate 3-Nitrobenzaldehyde (3.0 g, 20 mmoles), ethyl 3-amino-2-butenoate (2.6 g, 20 mmoles) and ethyl 4,4,4-trifluoro-3-oxobutanoate (2.92 ml, 20 mmoles) were heated at reflux in ethanol (25 ml) for 6 hours. The solvent was removed in vacuo and the residue crystallised by the addition of ether/petroleum ether (60°–80°). The resulting solid was recrystallised from ether/petroleum ether (60°–80°) to give the title compound as colourless crystals (1.9 g) mp 120°–1°.

EXAMPLE 2

3-Ethyl 5-methyl 4-(2,3-dichlorophenyl)-1,2,3,4-tetrahydro-2-hydroxy-6-methyl-2-(trifluoromethyl)-3,5-pyridinedicarboxylate Prepared by the method of Example 1. Two isomeric compounds were obtained. Isomer 1 recrystallised from cyclohexane mp 140°–1°. Isomer 2 recrystallised from cyclohexane mp 118°–9.5°.

EXAMPLE 3

Diethyl 1,2,3,4-tetrahydro-2-hydroxy-6-methyl-4-(3-nitrophenyl)-2-(pentafluoroethyl)-3,5-pyridinedicarboxylate Prepared by the method of Example 1. Two isomeric compounds were obtained. Isomer 1 recrystallised from 2-propanol mp 103°–4°. Isomer 2 recrystallised from 2-propanol mp 121°–2°.

EXAMPLE 4

Diethyl 1,2,3,4-tetrahydro-2-hydroxy-6-methyl-4-(3-nitrophenyl)-2-(trichloromethyl)-3,5-pyridinedicarboxylate (a) Ethyl 4,4,4-trichloro-2-(3-nitrophenylmethylene)-3-oxobutanoate 3-Nitrobenzaldehyde (7.55 g, 50 mmoles), ethyl 4,4,4-trichloro-3-oxobutanoate (18.33 g, 59.5 mmoles), piperidine (0.66 ml) and hexanoic acid (0.33 ml) were heated at reflux in toluene (130 ml) for 48 hours using a Dean and Stark apparatus. The mixture was cooled, evaporated to dryness in vacuo and crystallised by trituration with ethyl acetate/petroleum ether (60°–80°). Recrystallisation from 2-propanol gave the sub-title compound (5.3 g) mp 105.5°–7°.

(b) Diethyl 1,2,3,4-tetrahydro-2-hydroxy-6-methyl-4-(3-nitrophenyl)-2-(trichloromethyl)-3,5-pyridinedicarboxylate Ethyl 4,4,4-trichloro-2-(3-nitrophenylmethylene)-3-oxobutanoate (7.19 g, 0.02 mmoles) and ethyl 3-amino-2-butenoate (2.53 g) were heated at 60° for 24 hours in tert-butanol (60 ml). The solvent was evaporated and the residue chromatographed on silica eluting with ether/petroleum ether (60°–80°) mixtures to give the title compound (4.04 g). Recrystallised from 2-propanol. mp 125°–6.5°.

The compounds of Examples 5 to 9 were prepared using appropriate starting materials and the method described in Example 4.

EXAMPLE 5

Diethyl 1,4-dihydro-2-methyl-6-phenyl-4-(2-(trifluoromethyl)phenyl)-3,5-pyridinedicarboxylate Recrystallisation from 2-propanol gave the title compound (3.7 g) mp 149°–150°.

EXAMPLE 6

5-Methyl 3-(1-methylethyl) 4-(4-benzofurazanyl)-1,4-dihydro-2-methyl-6-phenyl-3,5-pyridinedicarboxylate Recrystallised from 2-propanol to give the title compound mp 198°–200°.

EXAMPLE 7

5-Methyl 3-(1-methylethyl) 1,4-dihydro-2-methyl-6-phenyl-4-(2-(trifluoromethyl)phenyl)-3,5-pyridinedicarboxylate Recrystallised from petroleum ether (60°–80°) mp 111°–2°.

EXAMPLE 8

5-Ethyl 3-methyl 4-(2,3-dichlorophenyl)-1,2,3,4-tetrahydro-2-hydroxy-6-methyl-2-phenyl-3,5-pyridinedicarboxylate The title compound was obtained as a white solid. Nmr (D$_6$-DMSO)δ6.0(s,1H), 4.9(d,1H,J=11 Hz), 0.7(t,3H, J=7 Hz).

EXAMPLE 9

Diethyl 4-(4-benzofurazanyl)-2-diethoxymethyl-1,4,5,6-tetrahydro-6-hydroxy-6-(trifluoromethyl)-3,5-pyridinedicarboxylate The title product was obtained as an oil. M+ 531.

EXAMPLE 10

Diethyl 2-(fluoromethyl)-6-formyl-1,4-dihydro-4-(3-nitrophenyl)-3,5-pyridinedicarboxylate Ethyl 4,4-diethoxy-2-(3-nitrophenylmethylene)-3-oxobutanoate (21.75 g, 62 mmoles) and ethyl 3-amino-4-fluoro-2-butenoate (9.17 g, 68 mmoles) were heated at 125° for 1.5 hours. The reaction mixture was dissolved in ethyl acetate (150 ml), washed with water and saturated brine, dried (MgSO$_4$) and the solvent was removed in vacuo. The residue was dissolved in tetrahydrofuran (195 ml) and 50% aqueous hydrochloric acid (292 ml) was added slowly. After 30 minutes the reaction mixture was extracted with ethyl acetate and the organic extract washed with saturated aqueous sodium bicarbonate, water, dried (MgSO$_4$) and the solvent was removed in vacuo. The residue was chromatographed on silica eluting with ethyl acetate/petroleum ether (60°–80°) mixtures. Crystallisation from 2-propanol gave the title compound (4.6 g), mp 88°–90°.

EXAMPLE 11

3-Methyl 5-(1-methylethyl) 4-(4-benzofurazanyl)-1,2,3,4-tetrahydro-2-hydroxy-6-methyl-2-phenyl-3,5-pyridinedicarboxylate 4-Benzofurazancarboxaldehyde (2.96 g, 20 mmoles), methyl beta-oxobenzenepropanoate (3.56 g, 20 mmoles), piperidine (0.05 ml) and hexanoic acid (0.13 ml) were heated at reflux for 3 hours in benzene (50 ml) using a Dean and Stark apparatus. The reaction was cooled, diluted with ethyl acetate and washed in turn with water, brine and saturated sodium bicarbonate and dried (Na$_2$SO$_4$). The solvent was removed in vacuo and the residue dissolved in ethanol (6 ml). 1-Methylethyl 3-amino-2-butenoate (3.0 g) and diethylamine (0.6 ml) were added and the mixture heated at 60° for 34 hours. The reaction mixture was cooled, evaporated to dryness in vacuo and the residue was dissolved in 2-propanol and treated with charcoal. The charcoal was filtered off and the title compound (1.1 g) was obtained on addition of cyclohexane mp 132°–4°.

EXAMPLE 12

Diethyl 2-amino-6-(fluoromethyl)-1,4-dihydro-4-(3-nitrophenyl)-3,5-pyridinedicarboxylate Ethyl 4-fluoro-2-(3-nitrophenylmethylene)-3-oxobutanoate (0.6 g, 2.1 mmoles) and ethyl 3,3-diamino- 2-propenoate hydrochloride (0.34 g, 12.0 mmoles) were heated at reflux in ethanol (10 ml) and a solution of sodium (0.05 g) in ethanol (5 ml) was added over one hour. The resulting solution was heated at reflux for a further 10 minutes and then filtered hot. The ethanolic solution was evaporated to dryness in vacuo and the resulting solid triturated with 2-propanol. The resulting solid was chromatographed on silica eluting with ether/petroleum ether (60°–80°) mixtures to give pure title compound, mp 177°–8°.

EXAMPLE 13

Diethyl 2-(fluoromethyl)-1,4,5,6-tetrahydro-6-hydroxy-4-(3-nitrophenyl)-6-phenyl-3,5-pyridinedicarboxylate and Diethyl 2-(fluoromethyl)-1,4-dihydro-4-(3-nitrophenyl)-6-phenyl-3,5-pyridinedicarboxylate Ethyl alpha-(3-nitrophenylmethylene)-beta-oxobenzenepropanoate (1.66 g, 16.3 mmoles), ethyl 3-amino-4-fluoro-2-butenoate (0.75 g, 15.6 mmoles) and piperidine (0.06 ml) were heated at 60° in ethanol (1 ml) for 72 hours. The reaction mixture was cooled and diluted with ethanol. The solid was filtered off, dried and then chromatographed on silica eluting with ethyl acetate/petroleum ether (60°–80°) mixtures to give the hydroxy compound (0.43 g) mp 188°–90° (dec).

The ethanolic mother liquors were evaporated to dryness in vacuo, dissolved in methylene chloride and pyridine (0.58 ml), and trifluoroacetic anhydride (0.48 ml) was added with stirring. After 16 hours, the solution was washed with 5% aqueous acetic acid (3×10 ml), and saturated sodium bicarbonate, dried (Na$_2$SO$_4$) and the solvent was removed in vacuo. The residue was chromatographed on silica eluting with ethyl acetate/petroleum ether (60°–80°) mixtures. Recrystallisation from 2-propanol gave the dihydropyridine (0.31 g), mp 151°–2°.

EXAMPLE 14

3-Ethyl 5-methyl 4-(2,3-dichlorophenyl)-1,4-dihydro-2-methyl-6-phenyl-3,5-pyridinedicarboxylate Ammonia (0.5 ml, d=0.88) was added to a solution of methyl alpha-(2,3-dichlorophenylmethylene)-beta-oxobenzenepropanoate (2 g, 7.3 mmoles) and ethyl 3-amino-2-butenoate (0.77 g, 6.0 mmoles) in tert. butanol (8 ml) at 60°. The reaction was maintained at this temperature for 16 hours. The solvent was removed in vacuo and the residue was chromatographed on silica eluting with ethyl acetate/petroleum ether (60°–80°) mixtures. The title compound (0.25 g) was obtained after crystallisation from 2-propanol mp 185°–6°.

EXAMPLE 15

Diethyl 4-(4-benzofurazanyl)-2-diethoxymethyl-1,4-dihydro-6-trifluoromethyl-3,5-pyridinedicarboxylate A solution of diethyl 4-(4-benzofurazanyl)-2-diethoxymethyl-1,4,5,6-tetrahydro-6-hydroxy-6-(trifluoromethyl)-3,5-pyridinedicarboxylate (9.0 g, 17 mmoles), trifluoroacetic anhydride (4.77 ml, 34 mmoles) and pyridine (4.05 ml, 51 mmoles) in dry dichloromethane (100 ml) was stirred at room temperature. After 3 hours the solution was washed with water, 10% aqueous hydrochloric acid solution, brine and dried (MgSO$_4$). Evaporation of the solvent left crude sub-title compound as an oil (8.8 g). Nmr (CDCl$_3$) δ 6.1 (s,H), 5.6(s,H).

EXAMPLE 16

Diethyl 1,2,3,4-tetrahydro-2-hydroxy-6-methyl-4-(3-nitrophenyl)-2-(4-nitrophenyl)-3,5-pyridinedicarboxylate Ethyl 4-nitro-beta-oxobenzenepropanoate (4.74 g, 20 mmoles), ethyl 2-(3-nitrophenylmethylene)-3-oxobutanoate (5.26 g, 20 mmoles) and aqueous ammonia (2.2 ml, d0.88) were heated at reflux in ethanol (50 ml) for 1.5 hours. After cooling the product was filtered off and recrystallised from ethanol to give the title compound (2.6 g) mp 196°–7°.

The compounds of Examples 17 to 22 were prepared using appropriate starting materials and the method of Example 16.

EXAMPLE 17

5-Methyl 3-(1-methylethyl) 1,4-dihydro-2-methyl-4-(3-nitrophenyl)-6-phenyl-3,5-pyridinedicarboxylate mp 184.5°–185.5° (2-propanol).

EXAMPLE 18

Diethyl 1,2,3,4-tetrahydro-2-hydroxy-6-methyl-4-(3-nitrophenyl)-2-phenyl-3,5-pyridinedicarboxylate m.p. 213°–5°. (Ethanol).

EXAMPLE 19

Diethyl 2-(3,4-dichlorophenyl)-1,2,3,4-tetrahydro-2-hydroxy-6-methyl-4-(3-nitrophenyl)-3,5-pyridinedicarboxylate White solid mp 188°–9°. (Ethanol).

EXAMPLE 20

Diethyl 2-(4-chlorophenyl)-1,2,3,4-tetrahydro-2-hydroxy-6-methyl-4-(3-nitrophenyl)-3,5-pyridinedicarboxylate Yellow solid mp 175°–8°. (Ethanol).

EXAMPLE 21

3-Methyl 5-(1-methylethyl) 1,2,3,4-tetrahydro-2-hydroxy-6-methyl-4-(3-nitrophenyl)-2-phenyl-3,5-pyridinedicarboxylate mp 134°–5°. (2-Propanol).

EXAMPLE 22

Diethyl 2-(3-chlorophenyl)-1,2,3,4-tetrahydro-2-hydroxy-6-methyl-4-(3-nitrophenyl)-3,5-pyridinedicarboxylate mp 212°–4°. (Ethanol).

EXAMPLE 23

Diethyl 4-(4-benzofurazanyl)-2-formyl-1,4-dihydro-6-(trifluoromethyl)-3,5-pyridinedicarboxylate To a solution of diethyl 4-(4-benzofurazanyl)-2-(diethoxymethyl)-1,4-dihydro-6-(trifluoromethyl)-3,5-pyridinedicarboxylate (7.6 g, 14.5 mmoles) in tetrahydrofuran (100 ml) was added 25% aqueous hydrochloric acid solution (100 ml) and the resulting solution heated at reflux. After 1.5 hours the cooled solution was poured into ethyl acetate (200 ml). The organic phase was separated and washed with water, saturated aqueous sodium bicarbonate solution, brine and dried (MgSO$_4$). Evaporation of the solvent left an oil (7.5 g) which was purified by chromatography on silica (300 g) using ether-petroleum ether (60°–80°) as eluent. The major component was obtained as an oil which gave a solid on trituration with 2-propanol. Recrystallisation from 2-propanol gave the title compound (0.45 g) as yellow crystals mp 94°–5°.

EXAMPLE 24

Diethyl 4-(4-benzofurazanyl)-1,4-dihydro-2-(hydroxymethyl)-6-trifluoromethyl-3,5-pyridinedicarboxylate A solution of diethyl 4-(4-benzofurazanyl)-2-formyl-1,4-dihydro-6-(trifluoromethyl)-3,5-pyridinedicarboxylate (1.1 g; 2.5 mmoles) in dry ethanol (90 ml) was cooled to 0° and sodium borohydride (0.14 g; 3.7 mmoles) was added portionwise over 3 minutes. After 10 minutes, 10% aqueous hydrochloric acid was added dropwise to pH3, and the mixture concentrated in vacuo at room temperature. The resulting yellow oil was dissolved in ether (50 ml) and saturated aqueous sodium bicarbonate was added to pH9. The organic solution was separated, washed with saturated aqueous sodium bicarbonate solution, water, brine and dried (MgSO$_4$). Evaporation of the solvent left a yellow oil which was crystallised from 2-propanol to give the title compound (0.5 g) mp 110°–11°.

The compound of Example 25 was prepared using appropriate starting materials and the method of Example 24.

EXAMPLE 25

Diethyl 2-(fluoromethyl)-1,4-dihydro-6-hydroxymethyl -4-(3-nitrophenyl)-3,5-pyridinedicarboxylate mp 149°–50°. (2-Propanol).

EXAMPLE 26

Diethyl 2-cyano-6-(fluoromethyl)-1,4-dihydro-4-(3-nitrophenyl)- 3,5-pyridinedicarboxylate (a) Diethyl 2-(2,4-dinitrophenoxyiminomethyl)-6-(fluoromethyl)-1,4-dihydro-4-(3-nitrophenyl)-3,5-pyridinedicarboxylate The compound of example 10 (0.2 g, 10.5 mmoles) and 0-(2,4-dinitrophenyl)hydroxylamine (0.1 g, 10.5 mmoles) were dissolved in warm ethanol (5 ml) and c.hydrochloric acid (1 drop) was added. The reaction mixture was allowed to cool to room temperature, and then in ice, and the resulting solid filtered off (0.157 g), mp 150°–2°.

(b) Diethyl 2-cyano-6-(fluoromethyl)-1,4-dihydro-4-(3-nitrophenyl)-3,5-pyridinedicarboxylate The product of step (a) (0.45 g, 0.8 mmoles) was dissolved in 95% aqueous ethanol (20 ml) by heating, and then potassium hydroxide (10.16 ml of 0.2M in 95% aqueous ethanol) was added dropwise. The solution was heated at reflux for 3 hours and then the ethanol removed in vacuo. The residue was dissolved in water (75 ml), 5% aqueous sodium hydroxide (6 ml) and chloroform (100 ml). The aqueous layer was separated and extracted several times with chloroform. The combined extracts were washed with water, dried (MgSO$_4$) and the solvent was removed in vacuo. The residue was crystallised from 2-propanol to give the title compound (0.19 g) mp 147°–8° (dec.).

EXAMPLE 27

Diethyl 2,6-di-(fluoromethyl)-1,4-dihydro-4-(3-nitro-phenyl)-3,5-pyridinedicarboxylate 3-Nitrobenzaldehyde (1.51 g, 10 mmoles), ethyl 4-fluoro-3-oxo-butanoate (3 g, 20 mmoles) and aqueous ammonia (1.1 ml, d=0.88) in ethanol (15 ml) were heated at reflux for 14 hours more aqueous ammonia (0.55 ml) was added after 6 hours. The solvent was removed in vacuo and the residue was chromatographed on silica eluting with ether/petroleum ether (60°–80°) mixtures and the product obtained was recrystallised from 2-propanol to give the title compound as yellow crystals (0.4 g) mp 113°–4°.

Examples of Intermediates

EXAMPLE A

Methyl 4-fluoro-3-oxo-butanoate

Fluoroacetyl chloride (7.1 g, 73 mmoles) was added dropwise to a stirred solution of 2,2-dimethyl-1,3-dioxane-4,6-dione (10.65 g, 74 mmoles) and pyridine (16.85 ml, 210 mmoles) in methylene chloride (75 ml) keeping the temperature below 10°. After stirring for 16 hours at room temperature the solution was diluted with methylene chloride (100 ml and then washed with 1N hydrochloric acid (200 ml) and water (100 ml). The organic extract was dried (Na$_2$SO$_4$) and the solvent removed in vacuo. The residue was dissolved in methanol (150 ml) and the solution heated at reflux for 2.5 hours. Removal of the solvent followed by distillation at 60°–80° (bath temp)/14 mm Hg gave methyl 4-fluoro-3-oxobutanoate (6.4 g).

The compounds of Examples B and C were prepared using appropriate starting materials and the method of Example A.

EXAMPLE B

1-Methylethyl 4-fluoro-3-oxobutanoate
Colourless oil, bp 100°–120° (bath temp)/12 mm Hg.

EXAMPLE C

Tetrahydro-4H-pyran-4-yl 4-fluoro-3-oxobutanoate
Nmr (CDCl$_3$)δ5.0(m,H), 4.9(d,2H,J=48 Hz).

EXAMPLE D

2-Methoxyethyl 4-fluoro-3-oxobutanoate

Ethyl 4-fluoro-3-oxobutanoate (2.1 g) was heated at reflux in 2-methoxyethanol (10 ml) for 3 hours. The solvent was removed in vacuo and the residue distilled to give the title compound as a colourless oil (1.75 g). Nmr (CDCl$_3$)δ4.9 (d,2H,J-48 Hz), 3.4 (s,3H).

The compounds of Examples E and F were prepared using appropriate starting materials and the method of Example D.

EXAMPLE E

2-Propoxyethyl 4-fluoro-3-oxobutanoate

Nmr (CDCl$_3$)δ4.9 (d,2H,J=47 Hz), 0.9 (t,3H,J=7 Hz).

EXAMPLE F

2-Phenoxyethyl 4-fluoro-3-oxobutanoate

Nmr (CDCl$_3$)δ7.5–6.9 (m,5H), (4.9 d,2H,J=48 Hz).

EXAMPLE G

Methyl 3-amino-4-fluoro-2-butenoate

Ammonia was bubbled through a solution of methyl 4-fluoro-3-oxobutanoate (2.6 g) in methanol (26 ml) at 0° for 3 hours. After stirring overnight at room temperature the solvent was removed in vacuo and the residue distilled (bp 100 at 20 mm Hg) to give the title compound (1.3 g) Nmr (CDCl$_3$)δ4.9 (d,2H,J=48 Hz), 4.6 (s,H), (3.7 s,3H).

The compounds of Examples H to J were prepared using appropriate starting materials and the method of Example G.

EXAMPLE H

Ethyl 3-amino-4-fluoro-2-butenoate

M+ 147; nmr (D$_6$-DMSO)δ4.9 (d,2H,J=46 Hz), 4.5 (s,H).

EXAMPLE I

Tetrahydro-4H-pyran-4-yl 3-amino-2-butenoate

Colourless crystals mp 88°–90°.

EXAMPLE J

1-Ethylpropyl 3-amino-2-butenoate

Pale yellow oil, bp 143°–8°/12 mm Hg.

EXAMPLE K (S)-2,2,2-Trichloro-1-phenylethyl 3-oxobutanoate

Diketene (3.7 ml, 47 mmoles) was added slowly to a stirred mixture of (S)-alpha-(trichloromethyl) phenylmethanol (9.2 g, 41 mmoles) and triethylamine (0.05 ml) kept at 80°–90°. The mixture was maintained for 5 hours at 90°. The cooled reaction mixture was purified using HPLC eluting with methylene chloride/petroleum ether 60°–80° to give the title compound (11 g) as an oil. Nmr (CDCl$_3$)δ6.39 (s,H), 3.61 (s,2H), 2.31 (s,3H).

The compound of Example L was obtained by the same method.

EXAMPLE L 2,2,2-Trichloro-1-phenylethyl 3-oxobutanoate

Colourless solid, nmr (CDCl$_3$)δ6.39 (s,H), 3.61 (s,2H), 2.31 (s,3H).

EXAMPLE M

Tetrahydro-4H-pyran-4-yl 3-oxobutanoate

A solution of tetrahydro-4H-pyran-4-ol (1.6 ml, 16.8 mmoles) and 5-acetyl-2,2-dimethyl-1,3-dioxane-4,6-dione (3.0 g, 16.1 mmoles) in dry benzene (50 ml) was heated under reflux for 4 hours. The solvent was removed in vacuo and the residue distilled at 146°–151°/14 mm Hg to afford the title product as a colourless oil, 2.84 g. Nmr (CDCl$_3$)δ5.1 (m,H), 3.5 (s,3H).

The esters of Examples N to R were prepared using appropriate starting materials and the method of Example M.

EXAMPLE N

1-Ethylpropyl 3-oxobutanoate

Colourless oil, bp 128°–38° (bath temp)/14 mm Hg.

EXAMPLE O

1-Methyl-1-phenylethyl 3-oxobutanoate

Colourless oil, bp 108°–110° (bath temp)/0.03 mm Hg.

EXAMPLE P

Methylcyclopentyl 3-oxobutanoate

Colourless oil, bp 134°–145° (bath temp)/14 mm Hg.

EXAMPLE Q 4-(1-Diphenylmethylazetidinyl) 3-oxobutanoate

Pale yellow oil. M+ 323.

EXAMPLE R

3-Oxetanyl 3-oxobutanoate

Pale yellow oil 165°–70° (bath temp)/12 mm Hg.

EXAMPLE S

1-Chloro-4-fluoro-2-(trifluoromethyl)benzene

4-Chloro-3-(trifluoromethyl)benzenamine (19.5 g, 100 mmoles), water (40 ml) and c.hydrochloric acid (40 ml) were heated with stirring on a steam bath until a white solid formed. The mixture was cooled (ice-salt bath) and a solution of sodium nitrite (7 g, 101 mmoles) in water (15 ml) was added over 15 mins. After stirring for a further hour at 0°, tetrafluoroboric acid (30 g of 40% aqueous solution) was added dropwise over 15 minutes. After one hour the solid was filtered off, washed with water (10 ml), methanol (30 ml) and ether (30 ml) and then dried in vacuo. The dry compound was heated at 140°–180° until no more fumes were observed. The cooled residue was dissolved in ethyl acetate, washed with 5% aqueous sodium hydroxide, dried Na$_2$SO$_4$) and the solvent was removed in vacuo. The residue was distilled in vacuo (12 mmHg, oven temperature 50°–55°) to give the sub-title compound as a colourless oil (7.5 g). M+ 200/198; nmr (CDCl$_3$)δ7.8–7.2 (m).

EXAMPLE T

2-Chloro-5-fluoro-3-(trifluoromethyl)benzaldehyde and 3-Chloro-6-fluoro-2-(trifluoromethyl)benzaldehyde Butyl lithium (60.4 ml of 1.6M in hexane, 97 mmoles) was added with stirring over 1.5 hours under nitrogen to a solution of 1-chloro-4-fluoro-2-(trifluoromethyl)-benzene (17.8 g, 91 mmoles) in dry tetrahydrofuran (150 ml) at −73°. After a further 1.5 hours at this temperature, N-methyl-N-phenylformamide (10.86 ml, 90 mmoles) in dry tetrahydrofuran (20 ml) was added over 0.5 hours. After 15 minutes the reaction mixture was poured onto 10% aqueous sulphuric acid. The ethereal layer was separated, washed with saturated sodium bicarbonate, dried (Na$_2$SO$_4$) and the solvent evaporated. The residue was purified by HPLC eluting with ethyl acetate/petroleum ether 60°–80° mixtures. 2-Chloro-5-fluoro-3-(trifluoromethyl) benzaldehyde (0.5 g) was eluted first.

M+ 226/228; nmr (CDCl$_3$)δ10.5 (s,H).

Further elution afforded 3-chloro-6-fluoro-2-(trifluoromethyl)benzaldehyde (8.35 g).

M+ 226/228; nmr (CDCl$_3$)δ10.5 (q,H).

EXAMPLE U

2-Chloro-3-(trifluoromethyl) benzaldehyde Butyl lithium (36.4 ml of 1.6M in hexane) was added to a stirred solution at −65° of 1-chloro-2-(trifluoromethyl)-benzene (10 g) in dry tetrahydrofuran (100 ml) over 20 mins. After stirring for 1.5 hours at −65°, a solution of N-methyl-N-phenylformamide (6.85 ml) in tetrahydrofuran (30 ml) was added over 1 hour. The reaction mixture was left at this temperature for 1.5 hours and then allowed to reach room temperature. It was then poured onto 10% sulphuric acid, extracted with ether and the organic extract was washed with brine, dried (Na$_2$SO$_4$) and the solvent removed in vacuo. The residue was distilled (20 mmHg, oven temperature 100°–125°) the distillate was cooled, filtered and the solid washed with petroleum ether (60°–80°) to give the desired aldehyde (3.5 g) as a colourless solid. M+ 210/208, nmr (CDCl$_3$)δ10.75 (s,H).

EXAMPLE V

2,3-Dichloro-6-fluorobenzaldehyde

Butyl lithium (48 ml of 1.6M in hexane, 52.3 mmoles) was added with stirring over 1.5 hours under nitrogen to a solution of 1,2-dichloro-4-fluorobenzene (7.85 g, 47.6 mmoles) in dry tetrahydrofuran (120 ml) at −68°. The solution wa stirred at −68° for 2 hours and then N-methyl-N-phenylformamide (6.48 ml) in dry tetrahydrofuran (15 ml) was added over 1.5 hours. After a further 1.5 hours at −68°, the reaction mixture was poured into 10% aqueous sulphuric acid and ether. The ethereal layer was separated, washed with brine, dried (Na$_2$SO$_4$) and evaporated to give the desired aldehyde (8 g). M+ 196/194/192, nmr (CDCl$_3$)δ10.5 (s,H).

EXAMPLE W

|  | % w/w | Range % w/w |
|---|---|---|
| Compound of formula I | 5 | 1–20 |
| Microcystalline cellulose | 50 | 10–80 |
| Spray dried lactose | 37.75 | 10–80 |
| Magnesium stearate | 1 | 0.25–2 |
| Colloidal silicon dioxide | 0.25 | 0.1–1 |
| Cross linked sodium carboxy methyl cellulose | 3 | 1–5 |
| Hydroxypropylmethylcellulose (coating) | 3 | 1–5 |

This formulation is made up as a direct compression tablet, or without compression or coating, may be filled into a gelatine capsule.

EXAMPLE X

|  | % w/w | Range % w/w |
|---|---|---|
| Compound of formula I | 5 | 1–20 |
| Microcystalline cellulose | 50 | 10–80 |
| Lactose | 35.75 | 10–80 |
| Polyvinylpyrrolidone | 2 | 1–5 |
| Magnesium stearate | 1 | 0.25–2 |
| Colloidal silicon dioxide | 0.25 | 0.1–1 |
| Cross linked sodium carboxy methyl cellulose | 3 | 1–5 |
| Hydroxypropyl methyl cellulose (coating) | 3 | 1–5 |

This formulation is made up as a granulate and then compressed into a tablet. Alternatively the granules may be filled into a gelatine capsule.

We claim:

1. A compound of formula

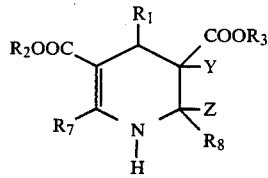

in which R$_1$ represents benzofurazanyl or phenyl, the phenyl being substituted by one or more of the groups halogen, nitro, —CN, —OR$_9$, —S(O)$_p$R$_9$, or alkyl C$_1$ to C$_6$ optionally substituted by halogen, p is 0, 1 or 2, R$_2$ and R$_3$, which may be the same or different, each represent hydrogen; alkyl C$_1$ to C$_6$ optionally substituted by one or more of the groups halogen, cyano, —XR$_4$, —NR$_5$R$_6$ or phenyl; cycloalkyl C$_3$ to C$_8$ optionally substituted by alkyl C$_1$ to C$_6$; an oxetanyl, azetidinyl, piperidinyl or tetrahydropyranyl ring which is optionally substituted by alkyl C$_1$ to C$_6$, the alkyl in turn optionally being substituted by one or more phenyl groups;

R$_5$ and R$_6$, which may be the same or different, each represent alkyl C$_1$ to C$_6$ optionally substituted by phenyl, Y and Z together form a bond, one of R$_7$ and R$_8$ represents alkyl C$_1$ to C$_6$ and the other represents phenyl, X is O or S, R$_4$ is alkyl C$_1$ to C$_6$ or phenyl, and R$_9$ is alkyl C$_1$ to C$_6$, provided that when R$_7$ is alkyl C$_1$ to C$_6$, R$_1$ represents 3-nitrophenyl and R$_2$ and R$_3$ are both ethyl, then R$_8$ does not represent phenyl, and pharmaceutically acceptable acid addition salts of those compounds containing a basic nitrogen atom.

2. A compound according to claim 1, in which R$_1$ is 4-benzofurazanyl, or phenyl substituted by nitro, chloro or —CF$_3$, and R$_2$ and R$_3$ are each alkyl C$_1$ to C$_3$.

3. A compound according to claim 1 and selected from

Diethyl 1,4-dihydro-2-methyl-6-phenyl-4-(2-(trifluoromethyl)phenyl)-3,5-pyridinedicarboxylate, 5-Methyl 3-(1-methylethyl) 4-(4-benzofurazanyl)1,4-dihydro-2-methyl-6-phenyl-3, 5-pyridinedicarboxylate, 5-methyl 3-(1-methylethyl) 1,4-dihydro-2-methyl-6phenyl-4-(2-(trifluoromethyl)phenyl)-3,5-pyridinedicarboxylate, 3-Ethyl 5-methyl 4-(2,3-dichlorophenyl)-1,4-dihydro-2-methyl-6-phenyl-3,5-pyridinedicarboxylate, and 5-Methyl 3-(1-methylethyl) 1,4-dihydro-2-methyl-4-(3-nitrophenyl)-6-phenyl-3,5-pyridinedicarboxylate.

4. A compound according to claim 1, in which R$_1$ is phenyl carrying at least two substituents selected from chloro, fluoro, —CF$_3$, methyl and nitro.

5. A compound according to claim 1, in which R$_1$ is benzofurazanyl.

6. A pharmaceutical formulation containing an amount of a compound according to claim 1 effective to treat renovascular, malignant or essential hypertension, pulmonary hypertension, vasospastic angina, chronic stable angina or congestive heart failure, in admixture with a pharmaceutically acceptable adjuvant, diluent or carrier.

7. A method of treatment of renovascular, malignant or essential hypertension, pulmonary hypertension, vasospastic angina, chronic stable angina or congestive heart failure, which comprises administering an effective amount of a compound according to claim 1 to a patient suffering from such a condition.

* * * * *